US012172950B2

(12) United States Patent
Bilz et al.

(10) Patent No.: US 12,172,950 B2
(45) Date of Patent: Dec. 24, 2024

(54) SALT-FREE PRODUCTION OF METHIONINE FROM METHIONINE NITRILE

(71) Applicant: Evonik Operations GmbH, Essen (DE)

(72) Inventors: Jürgen Bilz, Freigericht (DE); Cornelia Borgmann, Frankfurt (DE); Lucas Geist, Freigericht (DE); Harald Jakob, Hasselroth (DE); Martin Körfer, Kahl (DE); Christian Reus, Freigericht (DE); Daniel Rost, Lampertheim (DE)

(73) Assignee: Evonik Operations GmbH, Essen (DE)

( * ) Notice: Subject to any disclaimer, the term of this patent is extended or adjusted under 35 U.S.C. 154(b) by 767 days.

(21) Appl. No.: 17/420,886

(22) PCT Filed: Feb. 3, 2020

(86) PCT No.: PCT/EP2020/052613
§ 371 (c)(1),
(2) Date: Jul. 6, 2021

(87) PCT Pub. No.: WO2020/161074
PCT Pub. Date: Aug. 13, 2020

(65) Prior Publication Data
US 2022/0089534 A1    Mar. 24, 2022

(30) Foreign Application Priority Data
Feb. 4, 2019   (EP) ..................... 19155296

(51) Int. Cl.
| C07C 319/20 | (2006.01) |
| B01J 8/02 | (2006.01) |
| B01J 21/06 | (2006.01) |
| B01J 23/00 | (2006.01) |
| B01J 35/40 | (2024.01) |
| B01J 35/61 | (2024.01) |
| B01J 35/63 | (2024.01) |
| B01J 35/64 | (2024.01) |
| C07C 319/28 | (2006.01) |

(52) U.S. Cl.
CPC ............ *C07C 319/20* (2013.01); *B01J 8/02* (2013.01); *B01J 21/066* (2013.01); *B01J 23/002* (2013.01); *B01J 35/40* (2024.01); *B01J 35/612* (2024.01); *B01J 35/613* (2024.01); *B01J 35/615* (2024.01); *B01J 35/633* (2024.01); *B01J 35/651* (2024.01); *C07C 319/28* (2013.01); *B01J 2208/00017* (2013.01); *B01J 2208/00557* (2013.01)

(58) Field of Classification Search
None
See application file for complete search history.

(56) References Cited

U.S. PATENT DOCUMENTS

| 2001/0037038 A1 | 11/2001 | Ponceblanc et al. |
| 2003/0045753 A1 | 3/2003 | Ponceblanc et al. |
| 2019/0161434 A1 | 5/2019 | Aoki et al. |

FOREIGN PATENT DOCUMENTS

| EP | 3026038 A1 * | 6/2016 | ............ B01J 23/002 |
| JP | 3-93753 A | 4/1991 | |
| JP | 3-93754 A | 4/1991 | |
| WO | WO 01/60790 A1 | 8/2001 | |
| WO | WO 2018/021338 A1 | 2/2018 | |

OTHER PUBLICATIONS

International Search Report and Written Opinion issued Apr. 20, 2020 in PCT/EP2020/052613.

* cited by examiner

*Primary Examiner* — Amy C Bonaparte
(74) *Attorney, Agent, or Firm* — Oblon, McClelland, Maier & Neustadt, L.L.P.

(57) ABSTRACT

The invention refers to the use of a particulate catalyst containing 60.0 to 99.5 wt. % $ZrO_2$ stabilised with an oxide of the element Hf and at least one oxide of the element M, wherein M=Ce, Si, Ti, or Y, for the hydrolysis reaction of methionine amide to methionine, wherein the median particle size $x_{50}$ of the particulate catalyst is in the range of from 0.8 to 9.0 mm, preferably of from 1.0 to 7.0 mm. The invention also refers to a process for preparing methionine comprising a step of contacting a solution or suspension comprising methionine amide and water with said particulate catalyst to provide a reaction mixture comprising methionine and/or its ammonium salt from which methionine can be isolated.

20 Claims, No Drawings

SALT-FREE PRODUCTION OF METHIONINE FROM METHIONINE NITRILE

Due to their function as protein building blocks for the nutrition of animals and humans, amino acids have a fundamental importance in animal nutrition. Feedstuffs are therefore additionally enriched with amino acids such as D,L-methionine, which increases their nutritional value.

D,L-methionine is an essential amino acid that must be ingested with food. As a feed additive it contributes to an efficient, healthy and environmentally friendly nutrition of farm animals, especially poultry and pigs. It is therefore also an important building block when it comes to the sustainable supply of a growing world population with animal protein. Therefore, a cost-effective synthesis method for D,L-methionine, which is also well suited to large-scale industry, is of great importance.

STATE OF THE ART

On an industrial scale, methionine is chemically produced via the Bucherer-Bergs reaction, which is a variant of the Strecker synthesis. The starting substances 3-methylmercaptopropionaldehyde (MMP, produced from 2-propenal and methylmercaptan), hydrocyanic acid (hydrogen cyanide), ammonia and carbon dioxide are converted to 5-(2-methylmercaptoethyl)-hydantoin (methionine hydantoin). Hydrolysis of methionine hydantoin requires harsh conditions and stoichiometric amounts of a base, usually sodium hydroxide or potassium hydroxide or potassium carbonate. According to a well-known method, methionine is released from its sodium or potassium salt in the hydrolysate by neutralization with sulfuric acid, which can be filtered off as a precipitate from the mother liquor containing sodium or potassium sulphate. The by-product sodium or potassium sulphate must be recycled or disposed of elsewhere.

According to the well-known Degussa potassium carbonate cycle process, methionine is finally released from its potassium salt by treating the hydrolysate with carbon dioxide, whereby the methionine precipitate can be filtered out of the mother liquor containing potassium carbonate and potassium hydrogen carbonate (U.S. Pat. No. 5,770,769). The latter can be recovered, but a cycle of a large quantity of saline solution is required. Additionally, the conditions for methionine hydantoin formation and hydrolysis are harsh and energy-intensive with temperatures of up to over 200° C., so that there was still a need for a method that could be implemented on a large industrial scale and which has little or none of these disadvantages.

The production of methionine from methionine amide using various metal oxide catalysts has already been presented in several patent applications.

WO2001060788 A1 reveals an overall methionine process in which 2-amino-4-(methylthio)butanenitrile (methionine nitrile; MMP-aminonitrile; MMP-AN) is produced from 2-hydroxy-4-(methylthio)butanenitrile (MMP-Cyanohydrin, MMP-CN) and ammonia and hydrolysed by alkali metal hydroxide in the presence of acetone forming methionine amide which is in turn further hydrolysed to ammonium methioninate with the aid of a catalyst containing titanium, in particular titanium dioxide. From this, ammonia is released and expelled, so that solid methionine is obtained as the final product. Despite of a reaction temperature of 100° C. in the final step, the turnover is not complete, and the description does not allow any conclusions about the actual selectivity towards and yield of methionine in the reaction, so that undesirable residues of methionine amide remain in the final product (table 1, WO2001060788 A1).

An analogous overall process to methionine as described for WO2001060788 A1 is revealed in WO2001060789 A1, wherein the production of the titanium dioxide-containing catalyst used and also its use in the overall process for the production of methionine from methionine amide is disclosed. However, the turnover is 98%, but the description does not allow any conclusions about the actual selectivity towards and yield of methionine in the reaction.

Furthermore, an analogous overall process to methionine as described for WO2001060788 A1 is revealed in WO2001060790 A1, whereby the additional variant is shown here in which the alkali metal residues from the methionine amide stage are separated off only after hydrolysis of the methionine amide to form the methionine-ammonium/alkali metal salt mixture with an acidic ion exchange resin. Again, the turnover is 98%, but the description does not allow any conclusions about the actual selectivity towards and yield of methionine in the reaction.

In U.S. Pat. No. 6,417,395 B1, a similar overall process to methionine as in the above-mentioned WO publications is disclosed. However, the hydrolysis step from methionine amide to ammonium methioninate is carried out in the examples with the aid of titanium dioxide, ammonia or bacterial strains of *Corynebacterium Glutamicum* or *E. Coli*. With $TiO_2$-catalysis at 150° C., the yield of methionine is only 72% after a reaction time of 1.5 h.

In U.S. Pat. No. 6,545,179 B2, an overall process to methionine is also disclosed, wherein the hydrolysis step from methionine amide to ammonium methioninate is conducted in the examples with the aid of titanium dioxide catalysts. The usability of catalysts that comprise additional metals (Ti—W, Ti—Mo, Ti—Si—W, Ti—Nb—Mo, Ti—Zr, Ti—Al, Ti—Cr, Ti—Zn und Ti—V) was mentioned, however, neither any experimental instructions nor any results were disclosed in this regard.

JP03-093753 A reveals a process for the hydrolysis of amino acid nitriles to amino acid amides or amino acids. A corresponding amino acid nitrile is hydrolysed with at least one equivalent, preferably ten equivalents of water in the presence of 0.01-0.5 molequivalents (moleq) of a metal oxide from the group zirconium oxide, titanium oxide, niobium oxide, titanium oxide tungsten oxide, titanium oxide tin oxide, titanium oxide zinc oxide, at temperatures of 100-200° C. to give methionine amide. The subsequent hydrolysis step is carried out in the presence of a metal oxide from the group zirconium oxide, titanium oxide, niobium oxide, titanium oxide tungsten oxide, titanium oxide tin oxide and titanium oxide zinc oxide to give methionine. The yields for methionine with a zirconium oxide-titanium oxide-niobium oxide catalyst are at best 94% (example 1, JP03-093753 A). A disadvantage here, however, is the relatively high demand for catalyst, namely 100 g catalyst powder per 10 g amino acid amide as starting material (example 1, JP03-093753 A).

JP03-093754 A also discloses a process for the hydrolysis of amino acid nitriles to amino acid amides or amino acids. A corresponding amino acid nitrile is hydrolysed with at least one equivalent, preferably ten equivalents of water in the presence of 0.01-0.5 moleq of a metal oxide from the group titanium oxide-zirconium oxide, titanium oxide-alumina, titanium oxide-niobium oxide, titanium oxide-tungsten oxide, titanium oxide-tin oxide, titanium oxide-zinc oxide at temperatures of 50-220° C. The hydrolysis of the amino acid nitrile is carried out in the presence of 0.01-0.5 moleq of a metal oxide from the group titanium oxide-zirconium oxide, titanium oxide-alumina, titanium oxide-zinc oxide. In the case of hydrolysis of methionine amide to methionine, however, the methionine yields were only 93% (with titanium oxide-zirconium oxide) and 94% (with titanium oxide-niobium oxide) according to Examples 5 and 1 (JP03-093754 A), respectively, and the catalyst consumption was quite high (0.34 to 0.68 g catalyst per g of the amide).

JP03-093757 A reveals a process for the hydrolysis of amino acid nitriles to amino acid amides or amino acids. A corresponding amino acid nitrile is hydrolysed with at least one equivalent, preferably ten equivalents of water in the presence of 0.01-0.5 moleq of $ZrO_2$ and preferably additionally in the presence of a ketone, e.g. acetone, at temperatures of 50-220° C. However, the yields for methionine in the best case with commercially available zirconium oxide as catalyst and additional acetone are only 80% of theory. Another disadvantage here is the relatively high demand for additional acetone, namely 5.8 g acetone per 1 g catalyst powder per 10 g amino acid amide as starting material (example 1, JP03-093757 A).

According to the above-mentioned publications, so far mainly titanium dioxide-based catalysts have been used. The $ZrO_2$ catalysts used in the discussed publications showed significantly poorer performance and were not investigated with regard to their crystal modification or structure-property relationships. In the case of titanium dioxide catalysts, it is also known that only those with an anatase crystal modification catalyse the reaction from methionine amide to methionine. $TiO_2$ in rutile modification, however, shows no catalytic effect.

Finally EP3199519 A1 discloses a method for producing methionine, which comprises the step of contacting 2-amino-4-(methylthio)butanenitrile and water which each other in the presence of an oxide catalyst containing cerium (claim 1). The cerium containing catalyst is either a $CeO_2$ catalyst or a $CeO_2$—$ZrO_2$ mixed oxide catalyst, each in form of a fine powder. The yields of methionine reach from fair (60.9%, example 1) to very good (97.0%, example 4, EP3199519 A1). The reaction is performed at temperatures of from 60 to 100° C. according to the examples and residence times of from about 1 to 2 hours.

Additionally WO 2018/021338 discloses a method producing an alpha-amino acid by reaction of the corresponding alpha-amino acid amide with water in the presence of a zirconium compound and at least one further metal such as hafnium or cerium (claim 1). Herein specifically disclosed is the hydrolysis of methionine amide to methionine using a zirconium-containing complex metal oxide catalyst containing Hf, Ce, Y or Ti (examples 4, 5 and comparative examples 2, 3). However, it is neither disclosed the $ZrO_2$ content of the complex metal oxide catalyst nor the particle size or any other feature concerning the morphology of the catalyst. Furthermore, concerning the continuous method the document only discloses that a continuous tank type and a tubular reactor can be used also referred to as continuous stirred tank reactor (CSTR) and plug flow reactor (PFR) [0089]. However, both types are slurry reactors which are not suitable for a large-scale industrial process like the process for the production of methionine due to its complicated operation mode. The examples also do not provide a procedure which can be used in a continuous production because they are all conducted batch-wise, e.g., in a steel-made pressure vessel having a stirrer put thereinto (example 1).

Objective of the Invention

The underlying objective of this invention was therefore to provide a simplified chemical process for the production of D,L-methionine, in which less harsh and less salt-accumulating conditions than in the classical method of saponification of methionine hydantoin are made possible. The objective in this context was to provide a process for the salt-free preparation of D,L-methionine from D,L-methionine amide by metal oxide catalysis, which could then be coupled with a process for the neutral synthesis of D,L-methionine amide from D,L-methionine nitrile to form a salt-free overall process for the production of D,L-methionine. A further objective of this invention was to provide a highly active catalyst which at the same time could be used for the large-scale industrial process of the production of methionine.

Solution

This basic partial problem was solved by the use of a particulate catalyst containing 60.0 to 99.5 wt. % $ZrO_2$ stabilised with an oxide of the element Hf and at least one oxide of the element M, wherein M=Ce, Si, Ti, or Y, for the hydrolysis reaction of methionine amide to methionine, wherein the median particle size $x_{50}$ of the particulate catalyst is in the range of from 0.8 to 9.0 mm, preferably of from 1.0 to 7.0 mm.

Herein $ZrO_2$ stabilised with an oxide of the element Hf and at least one oxide of the element M means that it is substantially not a physical mixture of $ZrO_2$ and an oxide of the element Hf and at least one oxide of the element M, but it is a mixed oxide of Zirconium and Hafnium and at least an element M, which contains the given percentages of $ZrO_2$ and of an oxide of the element Hf e.g. $HfO_2$ and of at least one oxide of the element M as indicated in the claims and the description.

A preferred use of said catalyst is characterised in, that the particle size $x_{10}$ of the particulate catalyst is in the range of from 0.5 to 8.0 mm, preferably of from 0.8 to 6.5 mm, and the particle size $x_{50}$ of the particulate catalyst is in the range of from 1.0 to 11.0 mm, preferably of from 1.3 to 8.0 mm.

The use of such comparably coarse particulate catalyst material is very suitable for the continuous mode of production, because the catalyst material can be filled easily into a corresponding reactor, e.g. a reaction tube, wherein the rather wide passage opening between the particles allows a high throughput of the reaction liquid with additionally much lower system pressure compared e.g. with a fine powder catalyst, which is a great advantage.

The discussed $x_{10}$, $x_{50}$, and $x_{50}$ particle sizes of the particulate catalysts were measured by optical analysis according to ISO 13322-1:2014 and analysed also according to ISO 9276. The values $x_{10}$, $x_{50}$, and $x_{90}$ represent the particle sizes corresponding to 10%, 50%, or 90% of the cumulative undersize distribution by volume, respectively. This means, for example, that 10% by volume of the particulate catalyst is smaller than the $x_{10}$ particle size and 10% by volume of the particulate catalyst is larger than the $x_{50}$ particle size. The $x_{50}$ particle size thus corresponds to the median particle size, i.e. 50% by volume of the particles are smaller than this diameter and 50% are larger.

Unexpectedly, it was found that the catalysts according to the invention and not yet specified in the literature can catalyse the hydrolysis of methionine amide to methionine in an excellent way as shown in examples 13 to 19 (yield of methionine 86 to 100%). On the contrary, a particulate $ZrO_2$ catalyst stabilised with a metal oxide $La_2O_3$ or $WO_3$ with a median particle size $x_{50}$ of the particulate catalyst of 3.06 or 2.98 mm, respectively, does not promote the hydrolysis reaction of methionine amide to methionine comparably well as shown in examples 20 and 21 (yield of methionine 80% and 65%). Furthermore, comparative example A shows, that a $ZrO_2$-catalyst containing 81.3 wt. % $ZrO_2$, 1.7 wt. % $HfO_2$ and 17 wt. % $CeO_2$ and having a particle size $x_{50}$ of 0.6 µm, which is significantly below 0.8 mm results in yield of only 83% during hydrolysis of methionine amide to methionine.

On the contrary the example 13 conducted with a $ZrO_2$-catalyst having practically the same contents of $ZrO_2$ (81 wt. %), $HfO_2$ (1.7 wt. %) and $CeO_2$ (17.3 wt. %) but a much larger particle size $x_{50}$ of 3.06 mm und significantly larger BET-surface of 105 $m^2/g$ results in 100% conversion of methionine amide and 100% yield of methionine.

A particulate $ZrO_2$ catalyst (Comparative Example C) containing only $HfO_2$ (2 wt. %) and no other metal oxides also shows a very low hydrolysis activity and can therefore not be used according to the invention for the hydrolysis of methionine amide to methionine, even if other features are within the claim range of claim 1 (particle size ×50 4.95 mm). The methionine yield was only 16%.

A further comparison between an $HfO_2$— and $Y_2O_3$-stabilised $ZrO_2$ catalyst according to the invention (examples 4-8) with a state-of-the-art $TiO_2$ catalyst (examples 9-11) reveals that the catalysts used according to the invention are superior to the well examined $TiO_2$-containing catalysts previously used.

The catalysts used according to the invention can be manufactured from Zirconium oxide as a starting material according to the description of the process for the production of a mixed oxide containing zirconium and yttrium in EP 3026038 A1 (especially according to paragraph [0017], Examples 1-7) which is herewith incorporated by reference. Commercial zirconium sources usually contain about 0.5 to 3 wt. % Hf due to the natural association of Hf and Zr. The catalysts used according to the invention contain Hf which is also a stabilizer and are thus stabilised with an oxide of Hf and additionally with at least one oxide of the element M, wherein M=Ce, Si, Ti, or Y, indicating the formation of a mixed oxide phase rather than the mere physical mixing of the different metal oxides as also explained above. The catalysts preferably used according to the invention are characterised in that the element M=Si, Ti or Y, more preferably Si or Y.

The catalyst used in the process according to the present invention is not subject to any limitations regarding its preparation, provided that the preparation gives the particulate $ZrO_2$ based catalyst with the technical features according to the present invention.

The necessary starting material methionine amide can be produced by known methods such as the hydrolysis of methionine nitrile in the presence of a ketone and a base as catalysts or by metal oxide catalysis in the presence of ammonia. The latter route has the additional advantage that the use of the neutral catalyst for the hydrolysis of methionine amide in accordance with the invention provides a completely salt-free route to methionine from the usual precursor 3-methylmercaptopropionaldehyde (MMP).

In this context preferably used is a catalyst, containing from 0.1 to 40 wt. % of an oxide of the element Hf, Ce, Si, Ti, and Y, so that the main component of the active catalyst is $ZrO_2$.

More preferably used, however, is such a catalyst, which comprises 0.5 to 3 wt. % $HfO_2$ and additionally 0.1 to 40 wt. % $TiO_2$ and/or 0.2 to 6 wt. % $SiO_2$ and/or 3 to 10 wt. % $Y_2O_3$ and/or 5 to 25 wt. % $CeO_2$.

Most preferably used is such a catalyst, which comprises 1.5 to 2.8 wt. % $HfO_2$ and additionally 0.1 to 40 wt. % $TiO_2$ and/or 0.2 to 6 wt. % $SiO_2$ and/or 3 to 8 wt. % $Y_2O_3$ and/or 10 to 20 wt. % $CeO_2$.

As well preferably used is a catalyst, which has a BET surface area of from 30 to 250 $m^2/g$, preferably of from 50 to 160 $m^2/g$, particularly preferably of from 55 to 145 $m^2/g$. This also contributes to a satisfactory catalytic performance.

Additionally preferably used is a catalyst, which has an average pore volume of from 0.20 to 0.50 mL/g and particularly preferably of from 0.24 to 0.49 mL/g.

Also preferred is the use of a catalyst, which has a median pore diameter of from 20 to 200 nm, particularly preferably of from 23 to 160 nm.

Furthermore preferred is the use of a catalyst, which comprises triclinic or monoclinic $ZrO_2$. This can be derived from the comparison of examples 13 to 19 with 22 and 24 to 26.

It is also advantageous to use a catalyst additionally containing an inactive component as carrier and/or binder material, preferably $Al_2O_3$. In this way, both the catalyst activity can be suitably modified and zirconium can be saved at the same time.

The particulate catalyst used according to the invention is typically present in a shaped form, preferably as a granulate, extrudate, pellet or pressed product. It was quite astonishing that such a coarse material performed even better than powdered catalysts. This can be derived from the comparison of examples 13 to 19 with 22 to 27, A and E (powdered catalysts used having a particle size $x_{50}$ of from 0.5 µm to 0.4 mm). This is also a significant advantage, because primarily shaped form catalysts are technically feasible for the use in a large scale industrial production plant.

A further aspect of the invention is a process for preparing methionine comprising a step of contacting a solution or suspension comprising methionine amide and water with a catalyst having the features as defined above to provide a reaction mixture comprising methionine, the latter being primarily present in form of ammonium methioninate.

This process of preparing methionine by hydrolysing methionine amide is preferably conducted by contacting said solution or suspension comprising methionine amide with water and said catalyst at a temperature of from 70 to 200° C., more preferably of from 80 to 180° C., particularly preferably of from 90 to 160° C. and very particularly preferably of from 100 to 150° C. This ensures a high rate of turnover.

From a technical point of view the best range of the start concentration to be applied for said solution or suspension comprising methionine amide and water is a start concentration of from 1 to 30 wt. % methionine amide, preferably 2 to 24 wt. %, particularly preferably 3 to 20 wt. %.

Due to the fact that during the preceding reaction step of hydrolysing methionine nitrile to methionine amide mostly a certain percentage of methionine amide already continues to react to give methionine, said solution or suspension comprising methionine amide and water typically already contains 0 to 25 wt. % methionine, preferably 0 to 20 wt. % particularly preferably 0 to 15 wt. %.

If the preceding reaction step of hydrolysing methionine nitrile to methionine amide is conducted with the help of a ketone and a base as catalysts then said solution or suspension typically contains one or more ketone compound in a concentration of 0.1 to 2 moleq, preferably 0.5 to 1.5 moleq as well as an alkali metal or alkaline earth metal hydroxide in a concentration of 0.01 to 0.5 moleq, preferably 0.03 to 0.2 moleq, particularly preferably 0.05 to 0.1 moleq, relative to the methionine amide concentration (1 moleq) in said solution or suspension.

Because the formation of the precursor methionine nitrile is conducted with an excess of 1 to 10 moleq $NH_3$, a certain part of this excess may still be present even during the process according to the invention dependent on how much of it had been distilled off before. Thus, said solution or suspension typically contains $NH_3$ in a concentration of 0 to 10 moleq, preferably 0 to 7 moleq relative to the methionine amide concentration in said solution or suspension. This is not a disadvantage because $NH_3$ is able to accelerate the hydrolysis reaction of methionine nitrile to methionine amide and can be removed easily from the hydrolysate together with the liberated $NH_3$ of the hydrolysis of methionine amide.

Due to median particle size $x_{50}$ of the particulate catalyst in the range of from 0.8 to 9.0 mm, preferably of from 1.0 to 7.0 mm, it is especially advantageous that the reaction can be carried out in a continuous mode employing the catalyst in a fixed-bed type or trickle-bed type reactor. In this way, a largescale industrial application is feasible.

For a beneficial comparison of key performance parameters of the catalyst employed in a continuous reaction process, typically a flow rate, a residence time on the catalyst bed, or a weight-hourly-space-velocity (WHSV) can be utilised. In this case, the WHSV rate is the most accurate indicator, because for the calculation of the WHSV, the flow rate is set into relation to the amount of catalyst employed. The WHSV is thus determined by the feed of methionine amide per hour and per mass (=m) in g of catalyst employed (m(methionine amide)/h/m(catalyst)). If the process is carried out in a continuous mode, typically a WHSV of 0.0001 to 10, preferably 0.001 to 5, more preferably 0.01 to 1 and most preferably 0.025 to 0.1 g (methionine amide)/h/g (catalyst) is employed.

If the process is carried out in a batch mode, the catalyst is used in an amount of from 0.01 to 5 moleq $ZrO_2$ per mol methionine amide, preferably 0.05 to 2 moleq and particularly preferably 0.15 to 0.6 moleq.

A further aspect of the invention is a complete chemical process for preparing methionine comprising the following steps:
a. reacting methylmercaptopropionaldehyde with hydrocyanic acid and ammonia or reacting 2-hydroxy-4-(methylthio)butanenitrile with ammonia to provide a reaction mixture containing methionine nitrile,
b. optionally separation of all or a part of residual ammonia from the reaction mixture of step a.,
c. hydrolysing the reaction mixture obtained in step a. or b. in the presence of a carbonyl catalyst and a base catalyst and water or in the presence of a $CeO_2$ containing catalyst and water to provide a solution or suspension comprising methionine amide or a mixture of methionine amide and methionine,
d. optionally separating all or a part of the residual ammonia or residual ammonia and carbonyl catalyst from the solution or suspension of step c.,
e. preparing methionine by contacting the solution or suspension obtained from step c. or d. and water with a catalyst having the features as defined above,
f. optionally separating all or a part of the residual ammonia or residual ammonia and carbonyl catalyst from the solution or suspension of step e., preferably by distillation, to obtain a reaction liquid containing methionine and potentially some unreacted methionine amide,
g. isolation of the methionine by crystallisation and optionally subsequent re-crystallisation from the methionine containing reaction liquid obtained from step f. and obtaining a mother liquor
h. optionally recycling the mother liquor from step g. to step e. to complete the reaction of potentially unreacted methionine amide.

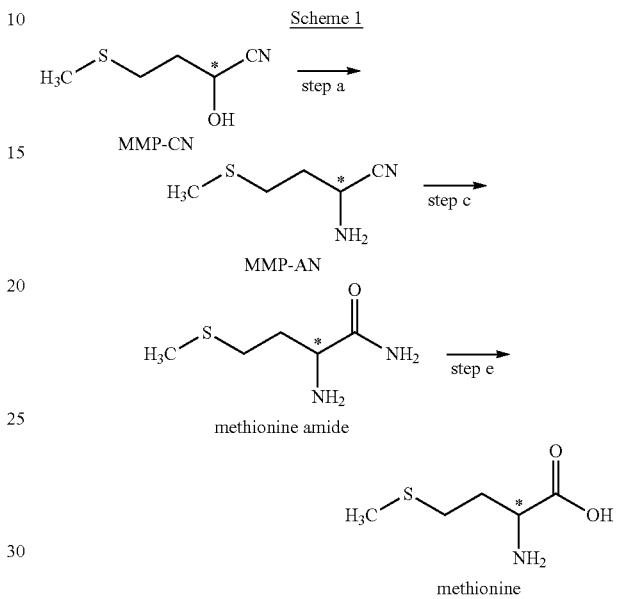

The particularly preferred method in step c., as exemplarily indicated in Scheme 1, is the hydrolysis of methionine nitrile to methionine amide with the aid of the neutral catalyst $CeO_2$ in addition to the use of the neutral catalyst containing $ZrO_2$ in the hydrolysis of methionine amide according to step e. because the salt accumulation can be completely avoided in this case.

The sole use of neutral catalysts in both hydrolysis steps c. and e. thus advantageously avoids the formation of waste salt substances and thus provides an overall salt-free process for the production of methionine, which is a considerable advantage, as explained above.

In the hydrolysis of methionine amide, the amide group is converted to the corresponding carboxylic acid group under release of ammonia. Thus, the hydrolysis of an equivalent of methionine amide is always accompanied by the release of an equivalent ammonia. Consequently, the final hydrolysis product methionine always contains ammonia, irrespective of the additional amount of ammonia in the methionine amide comprising starting solution or suspension as described above. However, the presence of ammonia in the methionine comprising product mixture inevitably leads to the formation of an ammonium salt of methionine. It is therefore not possible to obtain ammonia free methionine. Rather, the product mixture contains ammonium methioninate as the main product, and therefore, the so obtained product comprising methionine must be subjected to crystallization in order to obtain neutral methionine, i.e. ammonia free methionine.

The obtained primary ammonium methioninate as a temporary salt-like intermediate product can then be easily thermally split into methionine, which is produced and then easily isolated as a crystallisate, and volatile ammonia, which can easily be separated and returned as well, for example, to the methionine nitrile synthesis stage of step a. This crystallization step g. is already known from WO2015/039935 A1, especially disclosed on page 12 line 3 to page 13, line 3, FIG. 1 and in the examples 1 to 4, which is included by reference herewith.

If one selects the ketone- and base-catalysed hydrolysis variant for step c., which already works with clearly substoichiometric base quantities of, for example, 0.1 moleq KOH, a process with at least a low salt content is still available, which still represents a considerable improvement over the state of the art.

In cases in which the methionine amide is not completely converted to methionine, the unconverted methionine amide, which is much more water soluble than methionine can be easily separated from methionine within the crystallization step g. of the process described above. The mother liquor containing the methionine amide can conveniently be recycled to step e. or another contacting step according to step e. of the process described above in order to maximise the conversion to methionine. This applies for instance to an embodiment like the continuous example 35, wherein the methionine yield of 93% is quite high and the selectivity of 100% indicates that practically no by-products are formed, but about 7% of methionine amide remain unconverted and could be completely converted to methionine by this manner.

Thus, the invention provides a technical production process for methionine which, based on the available starting materials MMP, hydrocyanic acid and ammonia, leads to methionine at lower temperatures than in the current standard process via methionine hydantoin hydrolysis in high yields as well as with a simpler and salt-free process.

EXAMPLES

Analytical Methods
HPLC-Chromatography:

Chromatographic analyses of 2-hydroxy-4-(methylthio) butanenitrile (MMP-CN), 2-amino-4-(methylthio)butanenitrile (MMP-AN), 2-amino-4-(methylthio)butaneamide (methionine amide), 3-(methylthio)-1-propanone (MMP), and methionine (Met) were performed using HPLC systems from JASCO or Agilent with an RP-18 column (250×4.6 mm; 5 μm) and a subsequent UV detection at 210 nm. As eluent, a mixture consisting of 3.3 g $H_3PO_4$, 6.8 g $CH_3CN$, and 89.9 g $H_2O$ was used with a flow of 1 mL/min. 10 μL of the respective sample solution (50 mg sample in 25 mL $H_2O$) were injected into the eluent for analysis. Calibration was done in advance by injection of suitable standard stock solutions of the analyst and a subsequent comparison of peak areas with external standards as commonly done in organic chemical syntheses.

BET Surface Area

The BET surface areas were determined by physical adsorption of nitrogen on the surface of the solid and by calculating the amount of adsorbate gas corresponding to a monomolecular layer on the surface according to the Brunauer, Emmett, and Teller (BET) method. The samples used (0.2-0.9 g) were degassed at 150° C. for 20 min under vacuum prior to the measurement. The determination was then carried out at the temperature of liquid nitrogen (77 K). The amount of gas adsorbed was measured by a static-volumetric, 3-point measurement using a TriStar 3000 Miromeritics instrument. The method is described in general in DIN ISO 9277-5 (2003) and was being applied accordingly.

Particle Size Distribution of Powders

The particle size distribution of powders was measured by laser diffraction according to ISO 13320:2009 and analysed also according to ISO 9276 regarding their $x_{10}$, $x_{50}$, and $x_{50}$ particle sizes, representing the particle sizes corresponding to 10%, 50%, or 90% of the cumulative undersize distribution by volume, respectively. A spatula of sample material was added to 10 mL water+0.5 g/L tetrasodium pyrophosphate, ultrasonicated for 1 min and analysed with a LS 13320 laser diffraction spectrometer (Beckman-Coulter) with Universal Liquid Module (ULM).

Particle Size Distribution of Particulate Catalysts

The particle size distributions of particulate catalysts was measured by optical analysis of a series of catalyst particles (200 mL sample volume) using a CCD camera in a Camsizer (Retsch Technology GmbH) according to ISO 13322-1:2014 and analysed also according to ISO 9276 regarding their $x_{10}$, $x_{50}$, and $x_{50}$ particle sizes, representing the particle sizes corresponding to 10%, 50%, or 90% of the cumulative undersize distribution by volume, respectively.

X-Ray Powder Diffraction

X-ray powder diffraction (XRPD) is a non-destructive analytical technique for determination of crystalline phases in solid samples. XRPD measurements including the determination of the degree of crystallinity were conducted as follows. 0.5-2.0 g of the material were analysed in the Cubix$^3$ Pharma X-ray powder diffractometer from PANalytical using the following parameters:

X-ray tube: LFF-Cu X-ray tube, Cu Kα, λ=0.1542 nm
Generator settings: 40 mA, 40 KV
Detector: X'Celerator
Rotation: Yes/1 Rev./s
2-Theta range: 5°-100°
Step (° 2Θ) 0.0170
Time per step: 40 s The results were evaluated by using the current version of the PANalytical HighScore Plus software and up-to-date version of the ICDD database with crystalline reference phases.

X-Ray Fluorescence Analysis

X-ray fluorescence analysis (XRF) is a non-destructive analytical technique for determination of elemental composition in solid and liquid samples. In XRF, elements from F to U can be detected and quantified. For sample preparation, a small amount of the material was uniformly distributed on top of a thick layer of boreox (binding additive) in an aluminium cup and pressed into a flat powder pellet. The samples were analysed using a wavelength dispersive XRF spectrometer Axios from PANalytical using a UniQuant semi-quantitative application. The semi-quantitative evaluation was carried out using the Software UniQuant V 5. This software tool is based on the fundamental parameter algorithm; in this approach, a set of suitable calibration samples is measured and the measured intensities of the fluorescence lines are compared with the calculated intensities (the calculation is carried out using an established physical model).

Pore Analyses

The pore volume and median pore diameter was determined in accordance with DIN 66134 ($N_2$-sorption according to Barret, Joyner, Halenda).

Exemplary Preparation of Catalysts Used (not Part of the Invention)

The catalysts used according to the present invention are not subject to any limitation regarding their preparation, provided that the procedure used for their preparation gives catalysts with the features as those used according to the present invention. For example, the catalysts used in examples 13-19, table 3, according to the present invention were prepared in accordance to the published patent application EP 3026038 A1 and analysed regarding the following analytical parameters (results in table 3): $x_{10}$, $x_{50}$, and $x_{50}$ particle sizes, Brunauer, Emmett, and Teller (BET) surface area, X-ray powder diffraction (XRPD), X-ray fluorescence analysis (XRF, elemental composition), pore volume and median pore diameter.

For example, the $ZrO_2$-catalyst stabilised with 4 wt. % $Y_2O_3$ and containing 2 wt. % $HfO_2$ which was used for examples 4-8, 12, 16, 28-37 was prepared according to example 1 of the published patent application EP 3026038 A1:

Thus, the pore volume of 1215 g zirconium hydroxide particles (containing 1.6 wt. % $HfO_2$) XZO 1501/09 from MEL Chemicals was determined to 850 mL. 136 g $Y(NO_3)_3 \times 6 H_2O$ were dissolved in 263 g $H_2O$, resulting in a solution of 340 mL, which corresponds to 40% of the total pore volume. 380 g $H_2O$ were added to obtain a solution with a total volume of 680 mL, which corresponds to 80% of the total pore volume. The zirconium hydroxide material was impregnated in an Eirich intensive mixer type R by spraying the yttrium nitrate solution under moderate stirring conditions (215 rpm) onto the zirconium hydroxide for a period of 10 minutes. Subsequently, the wet powder was transformed into granules under stirring conditions (3000 rpm) for 1 hour. The material was sieved through a mesh sieving machine with mesh 2 to obtain granules with a particle size in the range of from 0.8 to 5 mm. Afterwards, the granules were dried at 120° C. for 2 hours and then calcined at 450° C. for 2 hours. The granules were sieved again through a mesh sieving machine with mesh 3 to obtain granules with a particle size in the range of from 0.8 to 2.5 mm. The mixed oxide contained 4 wt. % $Y_2O_3$. The obtained particles were analysed regarding the following analytical parameters (results in brackets): their $x_{10}$ (1.27 mm), $x_{50}$ (1.82 mm), and $x_{50}$ (2.43 mm) particle sizes, Brunauer, Emmett, and Teller (BET) surface area (125 m²/g), X-ray powder diffraction (XRPD, triclinic crystalline phase), X-ray fluorescence analysis (XRF, elemental composition 94 wt. % $ZrO_2$, 2 wt. % $HfO_2$, 4 wt. % $Y_2O_3$), pore volume (0.4 mL/g) and median pore diameter (30 nm), as also depicted in example 16, table 3.

Example 1 (not Part of the Invention): Synthesis of 2-amino-4-(methylthio)butanenitrile Starting from 2-hydroxy-4-(methylthio)butanenitrile 10.1 g 2-hydroxy-4-(methylthio)butanenitrile (MMP-CN; 90 wt. % in water, 69.3 mmol, 1 moleq) were mixed with 26.0 g $NH_3$ (32 wt. % in water, 7 moleq, 48.8 mmol) in a glass reactor and sealed subsequently. The light beige coloured and turbid emulsion containing 25 wt. % MMP-CN was stirred and heated to 50° C. for 30 minutes by means of a water bath. The obtained light yellow solution was analysed by HPLC chromatography confirming a 100% conversion of MMP-CN with a selectivity of 98.8% towards 2-amino-4-(methylthio)butanenitrile (MMP-AN; 67.2 mmol) and 2-amino-4-(methylthio)butaneamide (methionine amide; 1.2 mmol). Only traces of the iminodinitrile side-product 2,2'-bis-(2-methylmercaptoethyl)iminodiacetonitril (DN1, <0.1%), formed by reaction of MMP-CN with MMP-AN, as well as small amounts of 3-(methylthio)-1-propanone (MMP; <1%), formed by back reaction of MMP-CN to MMP and HCN, were observed.

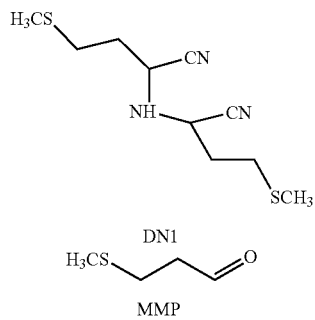

Example 2 (not Part of the Invention): Direct Conversion of the Obtained 2-amino-4-(methylthio) butanenitrile Towards a Mixture Comprising 2-amino-4-(methylthio)butaneamide and Methionine Using a $CeO_2$ Catalyst To the reaction solution obtained according to example 1 comprising 8.75 g MMP-AN (67.2 mol), 0.18 g methionine amide (1.2 mmol), 7.14 g $NH_3$ (419 mmol, 6 moleq), and 19.9 g water, another 36.2 g water (MMP-AN concentration 12 wt. %) and 1.0 g (5.8 mmol, 0.09 moleq) $CeO_2$ catalyst, manufactured according to EP 1506940 B1, example 1, were added. The glass reactor was again sealed and heated to 60° C. for 30 minutes by means of a pre-heated water bath while the reaction was stirred. Subsequently, the reaction solution was rapidly cooled to room temperature and analysed by HPLC chromatography confirming a 100% conversion of MMP-AN with a selectivity of 70% to 2-amino-4-(methylthio)butaneamide (methionine amide; 47.0 mmol) and 30% to methionine (Met; 20.2 mmol).

Example 3 (not Part of the Invention): Direct Conversion of the Obtained 2-amino-4-(methylthio) butanenitrile Towards a Mixture of 2-amino-4-(methylthio)butaneamide and Methionine Using a Carbonyl Compound and Alkali Metal Hydroxide as Catalysts The reaction solution obtained according to example 1 comprising 8.75 g MMP-AN (67.2 mol), 0.18 g methionine amide (1.2 mmol), 7.14 g $NH_3$ (419 mmol, 6 moleq), and 19.9 g water was cooled to 35° C. 7 g water, 4.0 g acetone (68.8 mmol, 1 moleq), and 2.0 g of an aqueous 10 wt. % KOH (3.4 mmol, 0.05 moleq) were added (MMP-AN concentration 18 wt. %). The glass reactor was again sealed and kept at 35° C. for 90 minutes by means of a water bath while the reaction was stirred. Subsequently, the reaction solution was rapidly cooled to room temperature, ammonia and acetone were removed at 30° C. under vacuum. The obtained product was analysed by HPLC chromatography confirming a 100% conversion of MMP-AN with a selectivity of 98.6% to methionine amide (65.4 mmol) and Met (2.0 mmol).

Example 4-8: Conversion of Methionine Amide to Methionine in an Autoclave with a $ZrO_2$ Catalyst Under Varying Conditions The volatile components of the methionine amide containing solution obtained from examples 2 or 3, in particular acetone and ammonia, were removed and the mixture obtained was adjusted to the following composition by addition of water and/or 32 wt. % aqueous ammonia as described in table 1: methionine amide (11.2%), KOH (0-0.1 moleq), NH$_3$ (0.5-3.5 moleq). The reaction solution was transferred to a steel autoclave. The metal oxide catalyst (0.18 moleq ZrO$_2$-catalyst stabilised with 4 wt. % Y$_2$O$_3$ and containing 2 wt. % HfO$_2$, manufactured according to the exemplary catalyst preparation procedure above) was then introduced in the form of a particulate catalyst (e.g. pellets) in a catalyst basket to prevent the particles from being destroyed by stirring the reaction solution. The autoclave was closed and heated to the desired temperature (110-170° C.) according to table 1 or 2 within one hour under stirring. The progress of the reaction was monitored after 15 minutes by HPLC analysis and finally terminated after 90 min by rapid cooling to room temperature and subsequent HPLC analysis of the reaction mixture.

TABLE 1

Results with a ZrO$_2$ catalyst stabilised with 4 wt. % Y$_2$O$_3$

| Expl. | Temp. [° C.] | NH$_3$ [eq] | Yield [%] | Conversion [%] | Selectivity [%] | Conversion after 15 min [%] |
|---|---|---|---|---|---|---|
| 4 | 110 | 2 | 86.7 | 88 | 98.5 | 51.8 |
| 5 | 170 | 2 | 84.2 | 100 | 84.2 | 85.6 |
| 6 | 140 | 0.5 | 93.6 | 100 | 93.6 | 83.4 |
| 7 | 140 | 3.5 | 93.8 | 98.2 | 95.5 | 72.5 |
| 8 | 140 | 2 | 98.3 | 100 | 98.3 | 90.1 |

Example 9-11 (not Part of the Invention, for Comparison): Conversion of Methionine Amide to Methionine in an Autoclave with a TiO$_2$ Catalyst Under Varying Conditions The reaction was performed as described for examples 4-8 but instead of 0.18 moleq of the ZrO$_2$ catalyst, 0.27 moleq TiO$_2$ "Aerolyst 7711" from Evonik, Germany was employed.

TABLE 2

Results with a TiO$_2$ catalyst (not part of the invention, for comparison)

| Expl. | Temp. [° C.] | NH$_3$ [eq] | Yield [%] | Conversion [%] | Selectivity [%] | Conversion after 15 min [%] |
|---|---|---|---|---|---|---|
| 9 | 110 | 2 | 62.2 | 63.7 | 97.8 | 29.2 |
| 10 | 170 | 2 | 86.9 | 100 | 86.9 | 84.1 |
| 11 | 140 | 2 | 86.5 | 97.8 | 88.5 | 90.1 |

The comparison of the results in table 1 with those in table 2 reveals that the ZrO$_2$ catalyst stabilised with 4 wt. % Y$_2$O$_3$ and containing 2 wt. % HfO$_2$ performs significantly better than the TiO$_2$ catalyst with regard to conversion of starting material as well as selectivity to and yield of Methionine.

Example 12: Conversion of Methionine Amide to Methionine Using a ZrO$_2$ Catalyst Stabilised with 4 wt. %

Y$_2$O$_3$ and containing 2 wt. % HfO$_2$ The volatile components of the methionine amide containing solution obtained from examples 2 or 3, in particular acetone and/or ammonia, were removed and the mixture obtained was adjusted to the following composition by addition of water: Water (140 g), methionine amide (18.5 g, 0.125 mol), KOH (0.33 g, 0.0059 mol, 0.05 moleq), methionine (0.7 g, 0.005 mol, 0.4 moleq). 32 wt. % aqueous ammonia solution (15.0 g, 0.282 mol, 2 moleq) was added. The reaction solution was transferred to a steel autoclave. A particulate ZrO$_2$-catalyst stabilised with 4 wt. % Y$_2$O$_3$ (3.0 g, 0.024 mmol, 0.20 moleq) and containing 2 wt. % HfO$_2$, manufactured according to the exemplary catalyst preparation procedure above, was introduced into the autoclave in the form of catalyst pellets in a catalyst basket. The autoclave was closed, stirred continuously with the aid of a gas agitator and heated to 140° C. The progress of the reaction was monitored every 15 minutes by HPLC analysis and finally terminated after 90 minutes. The reaction solution was rapidly cooled by the addition of water and diluted to a total quantity of 660 g. HPLC analysis of this solution revealed a 100% conversion of methionine amide and a methionine content of 2.86%, corresponding to a total content of 18.9 g methionine (0.127 mol, 98.1% yield, 98.1% selectivity). For control purposes, the volatile components of the solution were removed at the rotary evaporator. The obtained off-white powder was weighed and analysed by HPLC, confirming the above measured values for conversion, yield, and selectivity of 100%, 98.1%, and 98.1%, respectively.

Example 13-19: Conversion of Methionine Amide to Methionine by Using Different Particulate ZrO$_2$ Catalysts The volatile components of the methionine amide containing solution obtained from examples 2 or 3, in particular acetone and/or ammonia, were removed and the mixture obtained was adjusted to a methionine amide concentration of 12.4%. 50 g of the reaction solution (6.2 g, 41.9 mmol methionine amide) was transferred to a steel autoclave and a particulate ZrO$_2$-catalyst according to table 3 (3.0 g, 0.024 mmol, 0.57 moleq) was introduced into the autoclave in a catalyst basket. The autoclave was closed, stirred continuously, and heated to 120° C. within 60 min. After 30 min, a sample was taken and analysed by HPLC analysis regarding the methionine amide conversion as well as yield and selectivity towards methionine.

Examples 20-27 and A-E (not Part of the Invention, for Comparison): Conversion of Methionine Amide to Methionine by Using Different ZrO$_2$ Catalysts The reaction was performed as described for examples 13-19 but the catalysts listed in table 4a and 4b were employed instead. The powder catalysts were not sieved in advance but used as received from commercial sources (e.g., Sigma Aldrich).

The comparison of the results in table 3 with those in table 4a reveals that the particulate ZrO$_2$ catalysts stabilised with CeO$_2$, Y$_2$O$_3$, SiO$_2$, or TiO$_2$, or TiO$_2$ and SiO$_2$, each also containing HfO$_2$, perform significantly better under the given conditions (86 to 100% yield of methionine, examples 13 to 19) than the particulate ZrO$_2$ catalysts HfO$_2$ and stabilised with La$_2$O$_3$ or WO$_3$ (65 to 82%, yield of methionine, examples 20, 21) with regard to conversion of starting material and yield of methionine.

The comparison of the results of table 3 with those in table 4a further reveals that the particulate catalysts containing ZrO$_2$ stabilised with Y$_2$O$_3$, SiO$_2$, or TiO$_2$, or TiO$_2$ and SiO$_2$, each also stabilised with HfO$_2$, perform significantly better under the given conditions (86 to 100% yield of methionine, examples 13 to 19) than the powder catalysts also stabilised with Y$_2$O$_3$, SiO$_2$ or TiO$_2$, each also containing HfO$_2$, (18 to 23% yield of methionine, examples 22 to 24) or powder catalysts containing $HfO_2$ and stabilised with CaO or $Sc_2O_3$ (18 to 25% yield of methionine, examples 25 to 27) which could not be expected.

In addition, the particulate catalysts used according to the invention in table 3 with a triclinic or monoclinic crystal phase turned out to be superior over the powder catalysts in table 4a and 4b (examples 22 to 26, A and E) with either, cubic, orthorhombic, or rhomboedric crystal phases.

The particulate catalysts used according to the invention in table 3 with BET surface areas of from 55 to 145 $m^2/g$ turned out to be superior over the powder catalysts in table 4a and 4b (examples 22 to 27, A and E) with BET surface areas of from <1 to 11 $m^2/g$.

The particulate catalysts used according to the invention in table 3 with pore volumes of from 0.24 to 0.49 mL/g and median pore diameters of from 23 to 160 nm turned out to be superior over the powder catalysts in table 4a and 4b (examples 22 to 27, A and E) with pore volumes of from 0 to 0.38 mL/g and median pore diameters of from 0 to 128 nm.

TABLE 3

Examples of conversion of methionine amide (Met-Amide) to methionine by using different particulate $ZrO_2$ catalysts after 30 min at 120° C.

| Example | Particle size $x_{10}$ (mm) | Median particle size $x_{50}$ (mm) | Particle size $x_{90}$ (mm) | BET surface area ($m^2/g$) | Total pore volume (mL/g) | Median pore diameter (nm) | Crystal phase | $ZrO_2$ wt. % | $HfO_2$ wt. % | $TiO_2$ wt. % | $SiO_2$ wt. % | $Y_2O_3$ wt. % | $CeO_2$ wt. % | Conversion Met-amide | Yield Met | Selectivity Met |
|---|---|---|---|---|---|---|---|---|---|---|---|---|---|---|---|---|
| 13 | 2.84 | 3.06 | 3.13 | 105 | 0.24 | 156 | Triclinic | 81 | 1.7 | — | — | — | 17.3 | 100% | 100% | 100% |
| 14 | 3.30 | 3.43 | 3.54 | 55 | 0.3 | 40 | Monoclinic | 98 | 1.6 | 0.15 | 0.25 | — | — | 100% | 98% | 98% |
| 15 | 5.82 | 6.18 | 6.48 | 83.7 | 0.44 | 29 | Triclinic | 60 | 1.8 | 38.2 | — | — | — | 100% | 96% | 96% |
| 16 | 1.27 | 1.82 | 2.43 | 125 | 0.4 | 30 | Triclinic | 94 | 2 | — | — | 4 | — | 99% | 86% | 87% |
| 17 | 1.08 | 1.31 | 1.55 | 145 | 0.49 | 23 | Triclinic | 93 | 2 | — | 5 | — | — | 97% | 97% | 100% |
| 18 | 3.12 | 3.20 | 3.30 | 134 | 0.25 | 98 | Triclinic | 90 | 2.7 | — | — | 7.3 | — | 93% | 93% | 100% |
| 19 | 2.92 | 2.98 | 3.03 | 133 | 0.3 | 75 | Triclinic | 94 | 1.6 | 1.2 | 3.2 | — | — | 92% | 92% | 100% |

TABLE 4a (not part of the invention, for comparison): Examples of conversion of methionine amide to methionine by using different $ZrO_2$ catalysts after 30 min at 120° C.

| Example | Particle size $x_{10}$ (mm; if not noted otherwise) | Median particle size $x_{50}$ (mm; if not noted otherwise) | Particle size $x_{90}$ (mm; if not noted otherwise) | BET surface area ($m^2/g$) | Total pore volume (mL/g) | Median pore diameter (nm) | Crystal phase | $ZrO_2$ wt. % | $HfO_2$ wt. % | $TiO_2$ wt. % |
|---|---|---|---|---|---|---|---|---|---|---|
| 20 | 2.92 | 2.98 | 3.04 | 114 | 0.26 | 25 | Triclinic, trace monoclinic | 83 | 1.5 | — |
| 21 | 2.98 | 3.06 | 3.17 | 114 | 0.25 | 39 | Triclinic | 90 | 1.6 | — |
| 22 | 0.1 | 0.4 | 1.1 | 3.2 | 0.015 | 12 | Cubic | 78 | 2 | — |
| 23 | 0.1 μm | 0.6 μm | 3.1 μm | 4.6 | 0 | 0 | Triclinic | 65.5 | 1.5 | — |
| 24 | 4 μm | 21 μm | 56 μm | <1 | 0 | 0 | Orthorhombic | 59.5 | 1.5 | 39 |
| 25 | 0.3 μm | 0.5 μm | 0.7 μm | 9.5 | 0 | 0 | Rhomboedric | 92 | 1.7 | — |
| 26 | 0.2 μm | 1.2 μm | 4.6 μm | 1.8 | 0 | 0 | Orthorohombic | 61 | 2 | — |
| 27 | 67 μm | 117 μm | 173 μm | <1 | 0 | 0 | Triclinic | 61 | 2 | — |

| Example | $SiO_2$ wt. % | $Y_2O_3$ wt. % | $WO_3$ wt. % | $La_2O_3$ wt. % | CaO wt. % | $Sc_2O_3$ wt. % | Conversion Met-amide | Yield Met | Selectivity Met |
|---|---|---|---|---|---|---|---|---|---|
| 20 | — | — | 15.5 | — | — | — | 82% | 80% | 98% |
| 21 | — | — | — | 8.4 | — | — | 65% | 65% | 100% |
| 22 | — | 20 | — | — | — | — | 20% | 18% | 90% |
| 23 | 33 | — | — | — | — | — | 25% | 23% | 92% |
| 24 | — | — | — | — | — | — | 19% | 18% | 95% |
| 25 | — | — | — | — | — | 6.3 | 41% | 25% | 61% |
| 26 | — | — | — | — | 37 | — | 22% | 18% | 82% |
| 27 | — | — | — | — | 37 | — | 21% | 20% | 95% |

TABLE 4b (not part of the invention, for comparison): Examples of conversion of methionine amide to methionine by using different $ZrO_2$ catalysts after 30 min at 120° C.

| Example | Particle size $x_{10}$ (mm; if not noted otherwise) | Median particle size $x_{50}$ (mm; if not noted otherwise) | Particle size $x_{90}$ (mm; if not noted otherwise) | BET surface area ($m^2/g$) | Total pore volume (mL/g) | Median pore diameter (nm) | Crystal phase | $ZrO_2$ wt. % | $HfO_2$ wt. % | $CeO_2$ wt. % | Conversion Met-amide | Yield Met | Selectivity Met |
|---|---|---|---|---|---|---|---|---|---|---|---|---|---|
| A | 0.3 μm | 0.6 μm | 0.8 μm | 11 | 0.38 | 116 | Monoclinic, tetragonal | 81.3 | 1.7 | 17 | 90 | 83 | 92 |
| B | 2.06 | 3.03 | 4.73 | <1 | <0.01 | n.a. | Monoclinic | 99.7 | — | | 15 | 1 | 7 |
| C | 3.83 | 4.95 | 6.06 | <1 | <0.01 | n.a. | Monoclinic, trace Tetragonal | 98 | 2 | | 23 | 16 | 70 |
| D | 5.14 | 9.19 | 10.06 | <1 | <0.01 | n.a. | Monoclinic, trace Tetragonal | 98 | 2 | | 19 | 16 | 83 |
| E | 8.4 μm | 18.9 μm | 32.6 μm | 5.9 | 0.27 | 128 | Monoclinic | 98 | 2 | | 22 | 20 | 87 | n.a. = not applicable

Example 28-34: Conversion of Methionine Amide to Methionine Using a Continuous Reaction Mode with a $ZrO_2$ Catalyst Under Varying Conditions A fixed-bed reactor with an inner diameter of 25 mm was filled according to table 5 with the amount of a $ZrO_2$-catalyst stabilised with 2 wt. % $HfO_2$ and 4 wt. % $Y_2O_3$, manufactured according to the exemplary catalyst preparation procedure above. The catalyst bed was fixed with inert glass wool and a filling of 50 g inert glass granules (diameter 2 mm) below and above the catalyst bed each in order to assure a pre-heated reaction solution to the desired temperature upon catalyst contact. The fixed bed-reactor was double walled and heated by means of an oil bath pumped through the outer mantle of the reactor. The temperature inside the reactor was monitored by a thermocouple inside the catalyst bed to assure the desired temperature according to table 5. The pressure in the reactor was fixed to 4 bara (8 bara for T=160° C.).

The volatile components of the methionine amide containing solution obtained from examples 2 or 3, in particular acetone and/or ammonia, were removed and the mixture obtained was adjusted to the following composition by addition of water and/or 32 wt. % aqueous ammonia as described in table 5. The solution was directly fed from the bottom to the fixed bed reactor with a WHSV rate according to table 5.

The reaction solution was cooled to room temperature after passing the fixed-bed reactor and analysed by HPLC chromatography regularly. After having achieved a steady-state (after about 24-48 h, three more HPLC analyses after additional 24 h, 48 h and 72 h were conducted regarding the conversion of methionine amide as well as yield of and selectivity towards Met. All three analyses were in each of the cases identical within the HPLC analysis error margin and thus only one of them is listed in table 5.

TABLE 5

Conversion of methionine amide (Met-Amide) to methionine by using different particulate $ZrO_2$ catalysts in a continuous reaction mode under varying conditions

| Ex. | catalyst inventory [g] | c(Met-amide) [wt. %] | resident time [min] | WHSV [g(Met-amide)/ h/g(catalyst)] | T [° C.] | $NH_3$ [eq] | X Met-Amide [%] | Y Met [%] | S Met [%] |
|---|---|---|---|---|---|---|---|---|---|
| 28 | 90 | 3 | 35 | 0.03 | 140 | 0 | 93 | 93 | 100 |
| 29 | 30 | 3 | 70 | 0.015 | 160 | 0 | 88 | 88 | 100 |
| 30 | 30 | 3 | 70 | 0.015 | 160 | 3 | 87 | 87 | 100 |
| 31 | 30 | 6 | 70 | 0.03 | 160 | 3 | 87 | 87 | 100 |
| 32 | 30 | 9 | 70 | 0.045 | 140 | 3 | 81 | 81 | 100 |
| 33 | 30 | 13 | 70 | 0.065 | 140 | 3 | 72 | 72 | 100 |
| 34 | 30 | 17 | 70 | 0.085 | 140 | 3 | 77 | 65 | 84 |

X = conversion;
Y = yield;
S = selectivity

Example 35: Evaluation of Catalyst Lifetime and Deactivation Behaviour Using a Continuous Reaction Mode for 24 Days A fixed-bed reactor with an inner diameter of 25 mm was filled with 90 g of a $ZrO_2$-catalyst stabilised with and 4 wt. % $Y_2O_3$ and containing 2 wt. % $HfO_2$, manufactured according to the exemplary catalyst preparation procedure above. The catalyst bed was fixed with inert glass wool and a filling of 50 g inert glass granules (diameter 2 mm) below and above the catalyst bed each in order to assure a pre-heated reaction solution to the desired temperature upon catalyst contact. The fixed bed-reactor was double walled and heated by means of an oil bath pumped through the outer mantle of the reactor. The temperature inside the reactor was being monitored by a thermocouple inside the catalyst bed to assure the desired temperature of 140° C. The pressure in the reactor was being fixed to 4 bara. The volatile components of the methionine amide containing solution obtained from examples 2 or 3, in particular acetone and/or ammonia, were removed and the mixture obtained was adjusted to a methionine amide concentration of 3.0 wt. % by addition of water. The solution was directly fed from the bottom to the fixed bed reactor with a flow rate of 90 mL/h, resulting in a resident time of 35 min and a weight hour space velocity (WHSV) rate of 0.03 g (methionine amide)/h/g (catalyst). This solution was fed to the fixed-bed reactor for 24 days without any changes in the catalyst performance as reported in example 28, table 5 (yield Met 93%, conversion methionine amide 93%, selectivity towards Met 100%).

This example shows that the catalyst being used in a continuous reaction mode is not deactivated within a period of at least 24 days. The methionine yield of 93% is quite high and the selectivity of 100% indicates that practically no by-products are formed.

Example 36 Direct Conversion of the Reaction Solution Obtained from Example 2 in a Continuous Reaction Mode The fixed bed reactor was prepared with the $ZrO_2$-catalyst as described in example 35 but instead of 90 g only 30 g of a $ZrO_2$-catalyst stabilised with 4 wt. % $Y_2O_3$ and containing 2 wt. % $HfO_2$, manufactured according to the exemplary catalyst preparation procedure above, was employed. The solution obtained from example 2 comprising 7.0 g methionine amide (47 mmol), 3.0 g Met (20 mmol), 7.47 g $NH_3$ (439 mmol, 6 moleq), and 56.0 g water (methionine amide concentration 10 wt. %; Met concentration 4 wt. %) was diluted with water to a methionine amide concentration of 5 wt. % and a Met concentration of 2 wt. % and directly fed from the bottom to the fixed bed reactor with a flow rate of 15 mL/h at 140° C., resulting in a resident time of 70 min and in a weight hour space velocity (WHSV) rate of 0.025 g (methionine amide)/h/g (catalyst).

After 72 h continuous running, the product stream was analysed by HPLC analysis and revealed a 79% conversion of methionine amide, due to the initially higher Met concentration, with a yield of 74% of Met and a selectivity of 94% towards Met.

Example 37: Direct Conversion of the Reaction Solution Obtained from a Reaction Similar to Example 2 in a Continuous Reaction Mode The fixed bed reactor was prepared with the $ZrO_2$-catalyst as described in example 36. In another reaction according to example 2, a reaction solution comprising 3.0 g methionine amide (20 mmol), 7.0 g Met (47 mmol), 7.47 g $NH_3$ (439 mmol, 6 moleq), and 56.0 g water (methionine amide concentration 4 wt. %; Met concentration 10 wt. %) was diluted with water to a methionine amide concentration of 2 wt. % and a Met concentration of 5 wt. % and directly fed from the bottom to the fixed bed reactor with a flow rate of 15 mL/h at 140° C., resulting in a resident time of 70 min and in a weight hour space velocity (WHSV) rate of 0.01 g (methionine amide)/h/g (catalyst).

After 72 h continuous running, the product stream was analysed by HPLC analysis and revealed a 65% conversion of methionine amide, due to the initially higher Met concentration, with a yield of 62% of Met and a selectivity of 96% towards Met.

The invention claimed is:

1. A method of catalyzing the hydrolysis reaction of methionine amide to methionine, the method comprising contacting a solution or suspension comprising methionine amide and water with a particulate catalyst to produce a reaction mixture comprising methionine,
wherein the particulate catalyst comprises:
60.0 to 99.5 wt. % $ZrO_2$;
an oxide of the element Hf; and
at least one oxide of the element M, wherein M is Ce, Si, Ti, or Y,
wherein the $ZrO_2$ is stabilized by the oxide of the element Hf and the at least one oxide of the element M, and
wherein the median particle size $x_{50}$ of the particulate catalyst is from 0.8 to 9.0 mm.

2. The method of claim 1, wherein the element M is Si, Ti, or Y.

3. The method of claim 1, wherein the particle size $x_{10}$ of the particulate catalyst is from 0.5 to 8.0 mm.

4. The method of claim 1, wherein the particulate catalyst comprises from 0.1 to 40 wt. % of the oxide of the element Hf and at least one of oxides of the elements Ce, Si, Ti, and Y.

5. The method of claim 1, wherein the particulate catalyst comprises:
0.5 to 3.0 wt. % $HfO_2$ and at least one selected from the group consisting of 0.1 to 40 wt. % $TiO_2$, 0.2 to 6 wt. % $SiO_2$, 3 to 10 wt. % $Y_2O_3$, and 5 to 25 wt. % $CeO_2$, each weight percentage relative to the weight of the particulate catalyst.

6. The method of claim 1, wherein the particulate catalyst has a BET surface area of from 30 to 250 m²/g.

7. The method of claim 1, wherein the particulate catalyst has an average pore volume of from 0.20 to 0.50 mL/g.

8. The method of claim 1, wherein the particulate catalyst has a median pore diameter of from 20 to 200 nm.

9. The method of claim 1, wherein the $ZrO_2$ is triclinic or monoclinic.

10. The method of claim 1, wherein the particulate catalyst further comprises an inactive component as a carrier and/or a binder material.

11. The method of claim 1, wherein the particulate catalyst has a shaped form.

12. The method of claim 1, wherein the solution or suspension is contacted with the particulate catalyst at a temperature of from 70 to 200° C.

13. The method of claim 1, wherein the solution or suspension comprises from 1 to 30 wt. % methionine amide.

14. The method of claim 1, wherein the solution or suspension further comprises at least one ketone compound at a concentration of from 0.1 to 2 moleq, relative to the methionine amide concentration in the solution or suspension.

15. The method of claim 1, wherein the solution or suspension further comprises an alkali metal or alkaline earth metal hydroxide at a concentration of from 0.01 to 0.5 moleq, relative to the methionine amide concentration in the solution or suspension.

16. The method of claim 1, wherein the solution or suspension optionally further comprises $NH_3$ at a concentration of from 0 to 10 moleq, relative to the methionine amide concentration in the solution or suspension.

17. The method of claim 1, wherein the reaction is carried out in a continuous mode employing the particulate catalyst in a fixed-bed type reactor or a trickle-bed type reactor.

18. The method of claim 1, wherein the reaction is carried out in a continuous mode with a weight-hourly-space-velocity (WHSV) rate of from 0.0001 to 10-g (methionine amide)/h/g (catalyst).

19. The method of claim 1, wherein the reaction is carried out in a batch mode, and the particulate catalyst is used in an amount of from 0.01 to 5 moleq $ZrO_2$ per mol methionine amide.

20. A process for preparing methionine, comprising:
a) reacting methylmercaptopropionaldehyde with hydrocyanic acid and ammonia or reacting 2-hydroxy-4-

(methylthio) butyronitrile with ammonia to provide a reaction mixture comprising methionine nitrile, b) optionally separating of all or a part of residual ammonia from the reaction mixture of a), c) hydrolysing the reaction mixture obtained in a) or b) in the presence of a carbonyl catalyst, a base catalyst, and water or in the presence of a $CeO_2$ comprising catalyst and water to provide a solution or suspension comprising methionine amide or a mixture of methionine amide and methionine, d) optionally separating all or a part of the residual ammonia or residual ammonia and carbonyl catalyst from the solution or suspension obtained from c), e) preparing methionine by contacting the solution or suspension obtained from c) or d) and water with a particulate catalyst comprising 60.0 to 99.5 wt. % $ZrO_2$;

an oxide of the element Hf; and at least one oxide of the element M, wherein M is Ce, Si, Ti, or Y, wherein the $ZrO_2$ is stabilized by the oxide of the element Hf and the at least one oxide of the element M, and wherein the median particle size $x_{50}$ of the particulate catalyst is in the range of from 0.8 to 9.0 mm, thereby obtaining a reaction liquid comprising methionine, f) optionally separating all or a part of the residual ammonia or residual ammonia and carbonyl catalyst from the reaction liquid comprising methionine prepared in e), g) isolating methionine by crystallization, and optionally subsequent recrystallisation, from the reaction liquid comprising methionine obtained from e) or f), thereby obtaining a mother liquor, and h) optionally recycling the mother liquor from g) into e) to react unreacted methionine amide.

* * * * *